United States Patent [19]

Bowler et al.

[11] Patent Number: 4,751,240

[45] Date of Patent: Jun. 14, 1988

[54] PHENOL DERIVATIVES

[75] Inventors: Jean Bowler, Sandbach; Graham C. Crawley, Macclesfield; Philip N. Edwards, Bramhall; Alasdair T. Glen, Macclesfield; Michael S. Large, Congleton; Brian S. Tait, Macclesfield, all of United Kingdom

[73] Assignee: Imperial Chemical Industries PLC, London, England

[21] Appl. No.: 726,824

[22] Filed: Apr. 24, 1985

[30] Foreign Application Priority Data

Apr. 27, 1984 [GB] United Kingdom ................ 8410900
Oct. 23, 1984 [GB] United Kingdom ................ 8426753

[51] Int. Cl.⁴ .................... A61K 31/235; A61K 31/10

[52] U.S. Cl. .................................... 514/510; 514/512; 514/520; 514/522; 514/524; 514/525; 514/530; 514/532; 514/533; 514/535; 514/539; 514/545; 514/546; 514/548; 514/562; 514/569; 514/602; 514/603; 514/616; 514/629; 514/648; 514/677; 514/681; 514/708; 514/709; 514/712; 558/46; 558/270; 558/411; 558/413; 558/414; 558/418; 558/420; 558/422; 558/423; 558/425; 560/10; 560/30; 560/108; 560/139; 560/427; 560/428; 562/427; 562/428; 564/83; 564/85; 564/154; 564/162; 564/222; 564/428; 568/28; 568/29; 568/31; 568/33; 568/34; 568/36; 568/37; 568/42; 568/43; 568/52

[58] Field of Search ....................... 568/28, 29, 34, 36, 568/33, 37, 31, 27, 43, 42, 47, 49, 52; 558/46, 411, 414, 420, 222, 270, 413, 415, 416, 418, 422, 423, 425; 560/30, 427, 139, 10, 100, 108; 564/83, 154, 162, 222, 308, 162, 222, 85, 428; 514/524, 525, 530, 532, 533, 535, 539, 545, 546, 548, 562, 603, 616, 648, 677, 712, 706, 708, 709, 710, 711, 510, 647, 657, 520, 522, 569, 618, 629, 681, 602, 512; 562/427, 428; 260/465 F, 463

[56] References Cited

U.S. PATENT DOCUMENTS

| | | | |
|---|---|---|---|
| 3,296,304 | 1/1967 | Tilley | 260/558 |
| 3,506,716 | 4/1970 | Peterli | 568/47 |
| 3,539,642 | 11/1970 | Pesterfield | 260/559 |
| 3,546,163 | 12/1970 | Peterli | 568/47 |
| 3,729,443 | 4/1973 | Peterli | 260/45.95 C |
| 3,993,683 | 11/1976 | Nickl et al. | 260/465 G |
| 4,055,539 | 10/1977 | Rosenberger | 260/810 |
| 4,136,197 | 1/1979 | Hubner et al. | 562/442 |
| 4,191,776 | 3/1980 | Nickl et al. | 260/465 D |
| 4,304,940 | 12/1981 | Wedemeyer et al. | 568/45 |
| 4,396,553 | 8/1983 | Klaus | 568/31 |

FOREIGN PATENT DOCUMENTS

| | | |
|---|---|---|
| 0124369 | 11/1984 | European Pat. Off. . |
| 1262367 | 2/1972 | United Kingdom . |

OTHER PUBLICATIONS

S. W. Landvatter and J. A. Katzenellenbogen, "Nonsteroidal Estrogens: Synthesis and Estrogen Receptor Binding Affinity of Derivatives of (3R*,3S*)-3,4-Bis(4-hydroxyphenyl)hexane(Hexestrol) and (2R*,3S*)-2,3-Bis(4-hydroxyphenyl)pentane (Norhexestrol) Functionalized on the Side Chain", J. Med. Chem. 1982, 25, pp. 1300–1307.

*Primary Examiner*—Mary E. Ceperley
*Attorney, Agent, or Firm*—Cushman, Darby & Cushman

[57] ABSTRACT

A phenol derivative of the formula $$NU—A—X—R^1$$

wherein NU is a defined phenolic nucleus including a phenyl-hydroxynaphthyl; hydroxyphenyl-naphthyl; phenyl-hydroxyindanyl, phenyl-hydroxybenzothienyl or mono-hydroxyphenyl-ethylene or vinylene nucleus; wherein A is alkylene, alkenylene or alkynylene which may be interrupted by phenylene or other linkages, wherein $R^1$ is hydrogen, or alkyl, alkenyl, alkynyl, cycloalkyl, halogenoalkyl, alkoxyalkyl, halogenoalkoxyalkyl, aryl or arylalkyl, or $R^1$ is joined to $R^2$, and wherein X is $—CONR^2—$, $—CSNR^2—$, $—NR^{12}CO—$, $—NR^{12}CS—$, $—NR^{12}CONR^2—$, $$—NR^{12}—\overset{\overset{NR^{22}}{\|}}{C}—NR^2—,$$

$—SO_2NR^2—$or $—CO—$, or, when $R^1$ is not hydrogen, is $—NR^{12}COO—$, $—(PO)R^213$ , $—S—$, $—SO—$or $—SO_2—$, wherein $R^2$ is hydrogen or alkyl, or $R^1$ and $R^2$ together form alkylene; wherein $R^{12}$ is hydrogen or alkyl, and wherein $R^{22}$ is hydrogen, cyano or nitro; or a salt thereof when appropriate. The compounds possess antioestrogenic activity and may be used for the treatment of hormone-dependent breast tumors or of anovulatory infertility.

9 Claims, No Drawings

PHENOL DERIVATIVES

This invention relates to new phenol derivatives which possess antioestrogenic activity.

Various antioestrogens are now known. Two such compounds, tamoxifen and clomiphene, are commercially available, and others, for example nafoxidine, trioxifene and a number of compounds with code-numbers such as Cl 628 and LY 117018, have been the subject of clinical trials. Many oestrogenic compounds are also known, and in particular oestrogens based on hexoestrol bearing an amidic function, of the general formula:

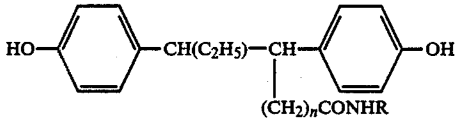

wherein n is 0 or 1 and R is hydrogen or alkyl, are described in the Journal of Medicinal Chemistry, 1982, 25, 1300–1307.

We have now found that certain phenol derivatives which are based on the hexoestrol nucleus but which bear an amidic or other function separated from the nucleus by an extended alkylene chain possess potent antioestrogenic activity.

According to the invention there is provided a phenol derivative of the formula:

$NU-A-X-R^1$ where NU is a phenolic nucleus of the general formula

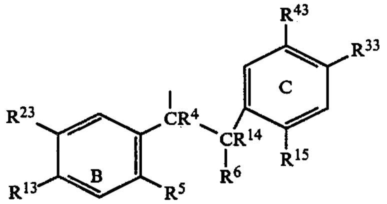

wherein one of $R^{13}$ and $R^{23}$, or one of $R^{33}$ and $R^{43}$, has the formula $R^3O-$, wherein $R^3$ is hydrogen or alkyl, cycloalkyl, alkanoyl, alkoxycarbonyl, carboxyalkanoyl or aroyl each of up to 10 carbon atoms;

wherein one of $R^{13}$ and $R^{23}$, or one of $R^{33}$ and $R^{43}$, which is in the other aromatic ring B or C from that which contains the $R^3O-$ substituent, is hydrogen, halogen, amino, trifluoromethyl, cyano, carboxy or carbamoyl, or alkyl, hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl each of up to 6 carbon atoms, and wherein the other two of $R^{13}$, $R^{23}$, $R^{33}$ and $R^{43}$ are hydrogen;

or wherein one of $R^{13}$ and $R^{23}$, and one of $R^{33}$ and $R^{43}$, is hydrogen, halogen, amino, trifluoromethyl, cyano, carboxy or carbamoyl, or alkyl, hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl each of up to 6 carbon atoms;

and wherein the other of $R^{13}$ and $R^{23}$, and the other of $R^{33}$ and $R^{43}$, is hydrogen;

wherein $R^4$ and $R^{14}$, which may be the same or different, each is hydrogen or alkyl of up to 5 carbon atoms, or $R^4$ and $R^{14}$ are joined together so that $CR^4-CR^{14}$ is an olefinic double bond;

wherein either $R^5$ and $R^{15}$ are both hydrogen and $R^6$ is alkyl of up to 5 carbon atoms;

or $R^5$ and $R^6$ together form a direct link or $-CH_2-$, $-CH(CH_3)-$, $-CH_2CH_2-$, $-(CH_2)_3-$, $-CH=CH-$, $-S-$, $-O-$, $-O-CR_2-$, $-O-CO-$, $-NR-CH_2-$ or $-N=CH-$ wherein R, the two values of which may be the same or different in $-OCR_2-$, is hydrogen or alkyl of up to 3 carbon atoms and $R^{15}$ is hydrogen;

or $R^{15}$ and $R^6$ together form $-CH_2-$ and $R^5$ is hydrogen;

and wherein the aromatic rings B and C each may optionally bear one or more halogen or alkyl substituents;

wherein A is straight- or branched-chain alkylene, alkenylene or alkynylene each of from 4 to 12 carbon atoms; or A has the formula:

$-A^1-Y^1-A^{11}-$ or $-A^1-Y^2-A^{21}-$ or
$-A^1-Y^3-A^{21}-$ wherein $A^1$ and $A^{11}$ are each alkylene or alkenylene having together a total of 3 to 11 carbon atoms and $Y^1$ is $-O-$, $-S-$, $-SO-$, $-SO_2-$ or $-CO-$; or $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^2$ is $-NRCO-$, $-CONR-$, $-COO-$ or $-OCO-$, wherein R has the meaning stated above, or $Y^3$ is phenylene, naphthylene or heterocyclene which may optionally bear one or more halogen or alkyl substituents, or heterocyclene which bears one or more alkoxy or oxo substituents, or A has the formula:

$-A^1-Y^1-A^{21}-Y^3-A^{31}-$ or
$-A^1-Y^3-A^{21}-Y^1-A^{11}-$ wherein $A^1$ and $A^{11}$ are each alkylene or alkenylene, and $A^{21}$ and $A^{31}$ are each a direct link or alkylene or alkenylene, such that $A^1$, $A^{21}$ and $A^{31}$ together, or $A^1$, $A^{21}$ and $A^{11}$ together, have a total of 1 to 9 carbon atoms, and $Y^1$ and $Y^3$ have the meanings stated above;

wherein $R^1$ is hydrogen, or alkyl, alkenyl, alkynyl, cycloalkyl, halogenoalkyl, alkoxyalkyl, halogenoalkoxyalkyl, aryl or arylalkyl each of up to 10 carbon atoms, or $R^1$ is joined to $R^2$ as defined below;

and wherein X is $-CONR^2-$, $-CSNR^2-$, $-NR^{12}CO-$, $-Nr^{12}CS-$, $-NR^{12}CONR^2-$ $NR^{22}$
||
$-NR^{12}-C-NR^2-$, $-SO_2NR^2-$ or $-CO-$, or, when $R^1$ is not hydrogen, is $-NR^{12}COO-$, $-(PO)R^2-$, $-S-$, $-SO-$ or $-SO_2-$, wherein $R^2$ is hydrogen or alkyl of up to 6 carbon atoms, or $R^1$ and $R^2$ together form alkylene such that, with the adjacent nitrogen atom, they form a heterocyclic ring of 5 to 7 ring atoms, one of which may be a second heterocyclic atom selected from oxygen, sulphur and nitrogen;

wherein $R^{12}$ is hydrogen or alkyl of up to 6 carbon atoms;

and wherein $R^{22}$ is hydrogen, cyano or nitro;

or a salt thereof when appropriate.

It will be observed that except when $R^4$ and $R^{14}$ are joined together so that $CR^4$—$CR^{14}$ is an olefinic double bond, the phenol derivative of the invention possesses at least two asymmetric carbon atoms, namely those which bear the substituents $R^4$ and $R^{14}$, and it can therefore exist in racemic and optically-active forms.

It is to be understood that this invention encompasses any racemic form of the phenol derivative, and any optically active form thereof, which possesses antioestrogenic activity, it being a matter of common general knowledge how a racemic compound may be separated into its optically-active forms, and how the antioestrogenic properties of any such form may be determined.

A suitable value for $R^{13}$, $R^{23}$, $R^{33}$ or $R^{43}$ when it is halogen or alkyl, or for the one or more optional halogen or alkyl substituents in ring B or C, or in the phenylene, naphthylene or heterocyclene group —$Y^3$— is, for example, fluoro, chloro, bromo, iodo, methyl, ethyl, isopropyl or isobutyl.

A suitable value for the optional alkoxy substituent in the heterocyclene group —$Y^3$— is, for example, methoxy or ethoxy.

A suitable value for $R^{13}$, $R^{23}$, $R^{33}$ or $R^{43}$ when it is hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl is, for example, hydroxymethyl, 1-hydroxyethyl, 2,2,2-trifluoro-1-hydroxy-1-trifluoroethyl, ethylamino, dimethylamino, acetamido, formyl, acetyl, propionyl, ethoxycarbonyl, methylcarbamoyl, diethylcarbamoyl, methylsulphamoyl, dimethylsulphamoyl or diethylsulphamoyl.

Preferably $R^{23}$ and $R^{43}$are hydrogen, $R^{13}$ has the formula $R^3O$— and $R^{33}$ is hydrogen or any of the other values stated above other than $R^3O$—.

A suitable value for $R^3$ when it is cycloalkyl, alkanoyl, alkoxycarbonyl, carboxyalkanoyl or aroyl is, for example, cyclopentyl, formyl, acetyl, propionyl, butyryl, pivaloyl, decanoyl, isopropoxycarbonyl, succinyl, glutaryl or benzoyl. $R^3$ is preferably hydrogen or alkanoyl or alkoxycarbonyl each of up to 5 carbon atoms, especially hydrogen.

A suitable value for R, $R^3$, $R^4$ or $R^{14}$ when it is alkyl is, for example, methyl or ethyl. R and $R^4$ are preferably hydrogen and $R^{14}$ is preferably hydrogen or methyl, or R is hydrogen and $R^4$ and $R^{14}$ are joined together.

A suitable value for $R^6$ when it is alkyl is, for example, methyl, ethyl or n-propyl.

A suitable value for the heterocyclene group —$Y^3$— is, for example, a mono- or bi-cyclic divalent heterocyclic group which contains 1, 2 or 3 heteroatoms selected from nitrogen, oxygen and sulphur atoms, which may be fully saturated, partially saturated or unsaturated, which may be fused to a benzene ring, and which may bear one or more halogen, alkyl, alkoxy or oxo substituents. The free bonds may be attached to carbon atoms or nitrogen atoms. Particular heterocyclene groups are, for example, thien-2,5-ylene, thien-2,4-ylene, pyrazol-1,4-ylene, thiazol-2,5-ylene, 1,3,4-thiadiazol-2,5-ylene, 1,3,4-oxadiazol-2,5-ylene, piperidine-1,4-diyl and 1,4-piperazine-1,4-diyl.

One preferred value for the group —A— is a straight-chain alkylene group of the formula $$-(CH_2)_n-$$

wherein n is an integer of from 4 to 12, especially from 5 to 11.

A second preferred value for the group A is a group of the formula $$-A^1-Y^3-A^{21}-$$

wherein $A^1$ is straight-chain alkylene or alkenylene each of 2 to 9 carbon atoms, especially alkylene of 3 to 6 carbon atoms, —Y— is phenylene (ortho, meta- or, especially, para-) and $A^{21}$ is a direct link, methylene, ethylene, trimethylene or vinylene, especially ethylene.

A suitable value for $R^1$ when it is alkyl, alkenyl, alkynyl, cycloalkyl or alkoxyalkyl is, for example, methyl, ethyl, n- propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3- dimethylbutyl, n-heptyl, n-decyl, n-undecyl, allyl, pent-3-ynyl, hex-3-ynyl, cyclopentyl, cyclohexyl or 3-ethoxypropyl.

A suitable value for $R^1$ when it is aryl or aralkyl is, for example, phenyl, o-ethylphenyl, p-chlorophenyl, m-chlorophenyl, p-cyanophenyl, p-hydroxyphenyl, p-methoxyphenyl, benzyl, alpha-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl or p-chlorophenethyl.

A suitable value for $R^1$ when it is halogenoalkyl or halogenoalkoxyalkyl is, for example, 2-chloro-2,2-difluoroethyl, 2,2,2-trifluoroethyl, 4,4,4-trifluorobutyl, 1H,1H-heptafluorobutyl, 5,5,5-trifluoropentyl, 4,4,5,5,5-pentafluoropentyl, 1H,1H,2H,2H -heptafluoropentyl, 6,6,6-trifluorohexyl, 5,5,6,6,6-pentafluorohexyl, 4,4,5,5,6,6,6-heptafluorohexyl, 1H,H,2H,2H-nonafluorohexyl, 5,5,6,6,7,7,7-heptafluoroheptyl or 3-(1,1,2,2-tetrafluoroethoxy)propyl.

A suitable value for the heterocyclic ring —$NR^1R^2$ is, for example, pyrrolidino, piperidino, 4-methylpiperidino, 3-methylpiperidino, morpholino or 4-methylpiperazino.

A suitable value for $R^2$ or $R^{12}$ when it is alkyl is, for example, methyl, ethyl or n-butyl.

One appropriate salt is an acid-addition salt of a phenol derivative which possesses a basic function, for example a compound wherein $R^5$ and $R^6$ together form —NR—$CH_2$— or —N=CH—. A suitable acid-addition salt is, for example, a hydrochloride, hydrobromide, acetate, citrate, oxalate or tartrate.

Another appropriate salt is a base-addition salt of a phenol derivative which possesses a carboxy function, for example a compound wherein $R^3$ is carboxyalkanoyl. A suitable base-addition salt is, for example, a sodium, potassium, ammonium or cyclohexylamine salt.

A preferred phenol derivative of the invention has the formula stated above wherein $R^3$, $R^{15}$, $R^{23}$ and $R^{43}$ are all hydrogen, wherein $R^{33}$ has any of the meanings stated above, wherein either $R^4$ is hydrogen and $R^{14}$ is hydrogen, methyl or ethyl, or $R^4$ and $R^{14}$ are joined together, wherein either $R^5$ is hydrogen and $R^6$ is methyl, ethyl or n-propyl, or $R^5$ and $R^6$ together form —$CH_2$—, —$CH_2CH_2$—, —$CH(CH^3)$—, —CH=CH— or —S—, wherein —A— is —$(CH_2)_n$—, wherein n is an integer from 4 to 12, especially from 5 to 11, or —A— is

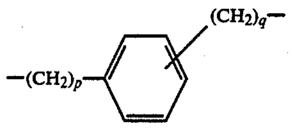

wherein p is an integer from 2 to 9, especially from 3 to 6, q is 0 to 3, especially 2, and the $-(CH_2)_q-$group is in the meta- or, especially, the para-position; wherein $R^1$ is alkyl or fluoroalkyl each of 4 to 10 carbon atoms, especially of 4 to 7 carbon atoms, or phenyl or chlorophenyl,or alkyl of 1 to 3 carbon atoms which bears a phenyl, tolyl, halogenophenyl or trifluoromethylphenyl substituent, or is linked to $R^2$ as stated below;

wherein X is $-CONR^2-$, $-S-$, $-SO-$ or $-SO_2-$, wherein $R^2$ is hydrogen or alkyl of up to 3 carbon atoms or together with $R^1$ forms alkylene of 5 or 6 carbon atoms;

and wherein ring C may optionally bear one or two methyl substituents.

A particularly preferred phenol derivative of the invention has the formula stated above wherein the number of carbon atoms in the two groups A and $R^1$ adds up to between 11 and 21, especially 14 to 16 if neither $R^1$ nor A contains a phenyl or phenylene group, 17 to 19 if there is either a phenylene group in —A— or a phenyl group in R, and 19 to 21 if there are both a phenylene group in —A— and a phenyl group in $R^1$.

An especially preferred phenol derivative of the invention has the formula $$NU-A-X-R^1$$

wherein NU is 6-hydroxy-2-phenylnaphth-1-yl, 1,2,3,4-tetrahydro-6-hydroxy-2-phenylnaphth-1-yl or 1,2,3,4-tetrahydro-6-hydroxy-2-methyl-2-phenyl-naphth-1-yl wherein the 2-phenyl group is unsubstituted or bears one methyl, ethyl, fluoro, chloro or dimethylsulphamoyl substituent, especially one 4-methyl substituent;

wherein A is $-(CH_2)_n-$ wherein n is 8, 9 or 10;

wherein X is $-S-$, $-SO-$ or $-SO_2-$; and wherein $R^1$ is straight-chain alkyl or fluoroalkyl of 4, 5, 6 or 7 carbon atoms.

Specific phenol derivatives of the invention are hereinafter described in the Examples. Of these, particularly preferred compounds are: (1RS,2RS)-1-(10-hexylsulphinyldecyl)-2-p-tolyl 1,2,3,4-tetrahydronaphth-6-ol and the corresponding 2-p-ethylphenyl and 2-p-fluorophenyl derivatives; (1RS,2RS)-1,2,3,4-tetrahydro-2-methyl-2-phenyl-1-[9-(4,4,5,5,5-pentafluoropentylsulphinyl)nonyl] naphthalene; and 2-p-tolyl-1-[9-(5,5,5-trifluoropentylsulphinyl)-nonyl]naphth-6-ol and the corresponding 9-(4,4,5,5,5-pentafluoropentylsulphinyl)-, (1H,H,2H,2H-heptafluoropentylsulphinyl) - and [3-(1,1,2,2-tetrafluoroethoxy)propyl]nonyl derivatives.

A preferred process for the manufacture of a phenol derivative of the invention wherein X has the formula $-CONR^2-$, $-CSNR^2-$ or $-SO^2NR^2-$ comprises the reaction of a compound of the formula $NU^1-A-Z^1$, wherein A has the meaning stated above, wherein $NU^1$ has the same meaning as stated above for NU except that the hydroxy group if present is protected and wherein $Z^1$ is an activated group derived from a carboxylic, thiocarboxylic or sulphonic acid, with an amine of the formula $HNR^1R^2$, wherein $R^1$ and $R^2$ have the meanings stated above, whereafter the protecting groups in $NU^1$ are removed by conventional means.

A suitable activated group $Z^1$ is, for example, a mixed anhydride, for example an anhydride formed by reaction of the acid with a chloroformate such as isobutyl chloroformate.

A suitable protecting group in $NU^1$ is, for example, an alkyl or aralkyl ether, for example the methyl or benzyl ether, or a tetrahydropyranyl ether, of both of the hydroxy functions. The methyl ether is preferred, and the methyl group is preferably removed with boron tribromide.

A preferred process for the manufacture of a phenol derivative of the invention wherein X has the formula —CO— comprises the reaction of an acid of the formula $NU^1-A-COOH$, wherein $NU^1$ and A have the meanings stated above, with an organometallic compound of the formula $R^1-M$, wherein $R^1$ has the meaning stated above and M is a metal group, for example the lithium group, whereafter the protecting groups in $NU^1$ are removed by conventional means.

A preferred process for the manufacture of a phenol derivative of the invention wherein X has the formula —S— or $-(PO)R^2-$ comprises the reaction of a compound of the formula $NU^1-A-Z^2$, wherein $NU^1$ and A have the meanings stated above and wherein $Z^2$ is a displaceable group, with a compound of the formula $R^1SH$, $R^1S-C(=NH)NH_2$ or $R^1R^2P-C_6H_5$, wherein $R^1$ and $R^2$ have the meanings stated above, whereafter the protecting groups in $NU^1$ are removed by conventional means, and whereafter a phosphonium salt is hydrolysed to the phosphinyl compound.

A suitable value for $Z^2$ is, for example a halogen atom, for example the bromine atom, or a sulphonyloxy group, for example the methanesulphonyloxy or toluene-p-sulphonyloxy group.

A preferred process for the manufacture of a phenol derivative of the invention wherein X has the formula $-NR^{12}CO-$, $-NR^{12}CS-$, $-NR^{12}CONR^2-$,

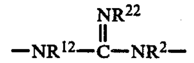

or $-NR^{12}COO-$ comprises the reaction of a compound of the formula $NU^1-A-NHR^{12}$, wherein $NU^1$, A and $R^{12}$ have the meanings stated above, with an acylating agent derived from an acid of the formula $R^1COOH$, $R^1CSOH$ or $R^1OCOOH$, or, for the manufacture of a urea, with an isocyanate of the formula $R^1NCO$; or, for the manufacture of a guanidine, with a cyanamide of the formula $R^1NR^2-CN$, whereafter the protecting groups in $NU^1$ are removed by conventional means.

A suitable acylating agent is, for example, an acyl chloride or acyl anhydride.

The starting materials for use in all the abovementioned processes may be obtained by elaborating the side-chain $-A-COOH$ or $-A^2-CH_2OH$ onto the nucleus $NU^1$ by conventional means. Detailed methods for carrying out such an elaboration are hereinafter provided in the Examples, but in general terms a compound of the formula:

$Z^2-A-COOR^7$ or
$Z^2-A^2-CH_2OSi(CH_3)_2C(CH_3)_3$ or $HC|C—A^{22}—CH_2OSi(CH_3)_2C(CH_3)_3$, wherein A and $Z^2$ have the meanings stated above, wherein $A^2$ is such that $—A^2CH_2—$ has the same meaning as A, wherein $A^{22}$ is such that $—CH_2CH_2A^{22}CH_2—$ has the same meaning as A, and wherein $R^7$ is hydrogen or alkyl of up to 6 carbon atoms, may be reacted with a suitable compound which is, or which may be converted into, $NU^1H$, or a compound of the formula:

$$NU^1—A^3—CHO$$

wherein $NU^1$ has the meaning stated above and wherein $A^3$ is a direct link or alkylene, may be reacted with a diethylphosphonate of the formula:

$$(C_2H_5O)_2\overset{O}{\overset{\|}{P}}CH_2—A^4—COOR^7$$

or a triphenylphosphonium bromide of the formula:

$$(C_6H_5)_3P^+CH_2—A^4—COOR^7\ Br^-$$

wherein $R^7$ has the meaning stated above and $A^4$ is alkylene or modified alkylene, to provide a compound of the formula:

$$NU^1—A^3—CH{=}CH—A^4—COOR^7$$

wherein $NU^1$, $A^3$, $A^4$ and $R^7$ have the meanings stated above. This can be used directly to provide a phenol derivative of the invention wherein A contains an olefinic double bond, or it may be reduced to provide a starting material for the preparation of a phenol derivative of the invention wherein $—A^3—(CH_2)_2—A^4—$ has the same meaning as A defined above.

The intermediate of the formula $$NU^1—A^2—CH_2OH$$

wherein $NU^1$ and $A^2$ have the meanings stated above, may be oxidised to the corresponding carboxylic acid of the formula $NU^1—A^2—COOH$ which provides the starting material for the first or second process of the invention described above; or it may be converted into a compound of the formula $NU^1—A^2—CH_2Z^2$ by reaction with a halogenating agent or a sulphonylating agent to provide the starting material for the third process of the invention described above.

The starting material for the fourth process of the invention described above may be obtained by using the third process of the invention described above except that an amine of the formula $R^{12}NH_2$ is used in place of a thiol of the formula $R^1SH$.

An alternative process for the manufacture of a phenol derivative of the invention wherein —A— is alkenylene of the formula $—A^3—CH{=}CH—A^4—$ comprises the reaction of a compound of the formula:

$$NU^1—A^3—CHO$$

wherein $NU^1$ and $A^3$ have the meanings stated above, with a triphenylphosphonium salt of the formula:

$$R^1X—A^4—CH_2—P^{30}(Ph)_3\ Q^{31}$$

wherein $R^1$, X and $A^4$ have the meanings stated above and wherein $Q^{31}$ is an anion, for example the bromide ion, whereafter the protecting groups in $NU^1$ are removed by conventional means.

The reaction may be carried out in solution in dimethyl sulphoxide in the presence of dimsyl sodium.

The phosphonium starting material may be obtained by reaction of triphenylphosphine with a bromide of the formula $$R^1—X—A^4—CH_2Br$$

A phenol derivative of the invention wherein the substituent $R^3$ is other than hydrogen may be obtained from the corresponding compound wherein the substituent $R^3$ is hydrogen by conventional etherification or esterification processes, and these may also be used in reverse to prepare the corresponding hydroxy compounds.

A phenol derivative of the invention wherein A is alkenylene may be hydrogenated to provide the corresponding compound wherein A is alkylene.

A phenol derivative of the invention wherein —X— is —CSNH— or —NHCS— may be obtained by the reaction of the corresponding compound wherein X is —CONH— or —NHCO— with 2,4-bis-(4-methoxyphenyl)-1,3-dithia-2,4-diphosphetane-2,4-disulphide.

A phenol derivative of the invention wherein X is —SO— or $—SO_2—$ may be obtained by the oxidation of the corresponding compound wherein X is —S—. The conditions for the oxidation will be chosen to provide the desired product; for example aqueous sodium metaperiodate solution will oxidise the sulphur group to sulphinyl, and m-chloroperbenzoic acid in chloroform solution will oxidise the sulphur group to sulphonyl.

A phenol derivative of the invention wherein $R^5$ and $R^6$ form $—CH_2CH_2—$ and either $R^4$ and $R^{14}$ are both hydrogen, or $R^4$ and $R^{14}$ are joined together so that $CR^4—CR^{14}$ is an olefinic double bond, may be converted into a phenol derivative of the invention wherein both $—CR^4—CR^{14}—$ and $—R^5—R^6—$ are $—CH{=}CH—$ (that is, a naphthalene derivative) by aromatisation by conventional means, for example with 2,3-dichloro-5,6-dicyano-1,4-benzoquinone.

As stated above, a phenol derivative of the invention possesses antioestrogenic activity. This may be demonstrated by its effect in antagonising the increase in weight of the uterus of an immature female rat produced by administering oestradiol benzoate to said rat. Thus, when a phenol derivative of the invention and oestradiol benzoate are co-administered for 3 days to such a rat, a smaller increase in uterine weight is produced than the substantial increase which would be produced by the administration of oestradiol benzoate without the phenol derivative of the invention.

In particular, a preferred phenol derivative of the invention produces an antioestrogenic effect at a dose which produces no partial agonist effect, unlike the known antioestrogens tamoxifen and clomiphene. When a preferred phenol is coadministered with oestradiol benzoate to a rat as described above, no increase in uterine weight whatsoever is observed at a suitable dose.

A compound with the above pharmacological properties is of value in the treatment of the same conditions in which tamoxifen is beneficial, in particular, in the treatment of anovulatory infertility and in the treatment of breast tumours. It is also of value in the treatment of menstrual disorders.

When used to produce an anti-oestrogenic effect in warm-blooded animals, a typical daily dose is from 0.1 to 25 mg/kg. administered orally or by injection. In man this is equivalent to an oral dose of from 5 to 1250 mg./day. A phenol derivative of the invention is most conveniently administered to man in the form of a pharmaceutical composition.

According to a further feature of the invention, there is provided a pharmaceutical composition comprising a phenol derivative of the invention together with a pharmaceutically acceptable diluent or carrier.

The composition may be in a form suitable for oral or parenteral administration. A tablet or capsule is a particularly convenient form for oral administration and such a composition may be made by conventional methods and contain conventional excipients. Thus a tablet could contain diluents, for example mannitol or maize starch, disintegrating agents, for example alginic acid, binding agents, for example methyl-cellulose, and lubricating agents, for example magnesium stearate.

The composition may contain, in addition to the phenol derivative of the invention, one or more other agents which antagonise or inhibit hormonal action, for example antiandrogenic agents, for example flutamide, antiprogestational agents, or aromatase inhibitors, for example aminoglutethimide.

A composition for oral administration may conveniently contain from 5 to 500 mg. of a phenol derivative of the invention.

The invention is illustrated but not limited by the following Examples:

EXAMPLE 1

A solution of (1RS, 2RS)-2-p-fluorophenyl-1,2,3,4-tetrahydro-1-(10-mesyloxydecyl)-6-methoxynaphthalene (0.4 g.) in dimethylformamide (2 ml.) was added to a stirred suspension of sodium hydride (0.16 g. of a 50% dispersion in mineral oil) and hexanethiol (0.404 $\mu$l.) in dimethylformamide (10 ml.) which had previously been stirred at laboratory temperature for 2 hours and the mixture was stirred at that temperature for 1 hour and then evaporated to dryness. Water (10 ml.) was added and the mixture was extracted three times with ethyl acetate (10 ml. each time). The combined extracts were dried and evaporated to dryness and the residue was purified by chromatography on a silica gel column using toluene as eluent.

Boron tribromide (0.66 ml. of a molar solution in methylene chloride) was added to a stirred solution of the (1RS,2RS)-2-p-fluorophenyl-1-(10-hexylthiodecyl)-1,2,3,4-tetrahydro-6-methoxynaphthalene thus obtained (0.11 g.) in methylene chloride (4 ml.) which was cooled to −70° C., and the mixture was allowed to warm up to laboratory temperature, stirred at that temperature for 16 hours and then poured onto ice (20 g.). The mixture was extracted three times with methylene chloride (10 ml. each time) and the combined extracts were washed with saturated aqueous sodium bicarbonate solution (5 ml.) and then with water, dried and evaporated to dryness. The residue was purified by chromatography on a silica gel column using toluene as eluent. There was thus obtained as an oil (1RS,2RS)-2-p-fluorophenyl-1-(10-hexylthiodecyl)-1,2,3,4-tetrahydronaphth-6-ol, the structure of which was confirmed by proton magnetic resonance and mass spectroscopy.

The (1RS,2RS)-2-p-fluorophenyl-1,2,3,4-tetrahydro-1-(10-mesyloxydecyl)-6-methoxynaphthalene used as starting material was obtained as follows:

A solution of p-fluorophenylacetic acid (3.9 g.) in tetrahydrofuran (30 ml.) was added to a stirred solution of lithium diisopropylamide [prepared from diisopropylamine (5.55 g.) in n-butyllithium (37 ml. of a 1.5 molar solution in hexane)]at −78° C., and the mixture was allowed to warm up to laboratory temperature, stirred at that temperature for 1 hour and then recooled to −70° C. A solution of 2-m-methoxyphenylethyl methanesulphonate (12.7 g.) in tetrahydrofuran (20 ml.) was added, the mixture was allowed to warm up to laboratory temperature and was stirred at that temperature for 16 hours and then evaporated to dryness. Water (70 ml.) was added to the residue and the mixture was washed three times with diethyl ether (70 ml. each time), acidified to pH 1 with aqueous 2N-hydrochloric acid and extracted three times with diethyl ether (70 ml. each time). The combined extracts were washed with water, dried and evaporated to dryness.

Oxalyl chloride (3.3 ml.) was added to a stirred solution of the 2-p-fluorophenyl-4-m-methoxyphenylbutyric acid thus obtained (6.7 g.) and dimethylformamide (0.05 ml.) in toluene (50 ml.) and the mixture was stirred at laboratory temperature for 2 hours and then evaporated to dryness. The residue was dissolved in methylene chloride (100 ml.), the solution was stirred and cooled to −20° C. and stannic chloride (3.2 ml.) was added. The mixture was stirred for 2 hours and then poured into ice-water (250 ml.) and the mixture was extracted three times with methylene chloride (100 ml. each time). The combined extracts were washed with saturated aqueous sodium bicarbonate solution and then with water, dried and evaporated to dryness and the residue was stirred with methanol. The mixture was filtered and there was thus obtained as solid residue 2-p-fluorophenyl-3,4-dihydro-6-methoxy -naphthalen-1(2H)-one, m.p. 124–127° C.

A solution of the above compound (0.54 g.) in tetrahydrofuran (5 ml.) was added to a boiling mixture of 10-(dimethyl-t-butylsilyloxy)dec-1-yne (1.6 g., prepared as described below) in tetrahydrofuran (20 ml.) and methyl magnesium chloride (1.38 ml. of a 2.9 molar solution in tetrahydrofuran) which had previously been heated under reflux for 1 hour under an atmosphere of argon, and the mixture was heated under reflux for 30 minutes, cooled and poured into ice-cold saturated aqueous ammonium chloride solution (10 ml.). The mixture was extracted three times with ethyl acetate (30 ml. each time) and the combined extracts were washed with water, dried and evaporated to dryness. There was thus obtained as residual oil 1-(10-dimethyl-t-butylsilyloxy -dec-1-ynyl)-2-p-fluorophenyl-6-methoxy-1,2,3,4-tetrahydronaphth-1-ol.

A solution of the above compound (0.5 g.) in ethyl acetate (10 ml.) was stirred with a 10% palladium-on charcoal catalyst (0.1 g.) under an atmosphere of hydrogen for 18 hours, filtered and the filtrate was evaporated to dryness. A mixture of the residue (0.5 g.), acetic acid (6.7 ml.), water (3.3 ml.) and tetrahydrofuran (3 ml.) was stirred at laboratory temperature for 18 hours and then evaporated to dryness and the residue was purified by chromatography on a silica gel column using a 4:1 v/v mixture of toluene and ethyl acetate as eluent. There was thus obtained 10-[(1RS,2RS)-2-p-fluorophenyl-6-methoxy-1,2,3,4-tetrahydronaphth-1-yl]decanol.

Methanesulphonyl chloride (0.10 ml.) was added to a stirred solution of the above decanol (0.42 g.) and triethylamine (0.21 ml.) in methylene chloride (10 ml.) which was maintained at −10° C. and the mixture was stirred at that temperature for 30 minutes and then poured into saturated aqueous sodium bicarbonate solution (5 ml.). The mixture was extracted three times with methylene chloride (10 ml. each time) and the combined extracts were dried and evaporated to dryness. The residue was purified by chromatography on a silica gel column using toluene as eluent. There was thus obtained (1RS,2RS)-2-p-fluorophenyl-1,2,3,4-tetrahydro-1-(10-mesyloxydecyl)-6-methoxynaphthalene.

The 10-(dimethyl-t-butylsilyloxy)dec-1-yne was obtained as follows:

A solution of dimethyl-t-butylsilyl chloride (18 g.) in tetrahydrofuran (50 ml.) was added dropwise to a stirred solution of 8-bromooctanol (20 g.) and imidazole (14.2 g.) in tetrahydrofuran (100 ml.) and the mixture was stirred at laboratory temperature for 3 hours, diluted with diethyl ether (200 ml.) and filtered. The filtrate was evaporated to dryness and the residue was purified by chromatography on a silica gel column using petroleum ether (b.p. 60–80° C.) as eluent. A solution of the 8-(dimethyl-t-butylsilyloxy)octyl bromide thus obtained (6.46 g.) in dimethyl sulphoxide (2 ml.) was added to a stirred suspension of lithium acetylide-ethylenediamine complex (2.02 g.) in dimethylsulphoxide (30 ml.) which was cooled to 10° C., and the mixture was stirred for 18 hours and then poured into ice-water (150 ml.). The mixture was extracted three times with petroleum ether (b.p. 60–80° C.; 30 ml. each time) and the combined extracts were washed with water (10 ml.), dried and evaporated to dryness. The residue was purified by chromatography on a silica gel column using a 5:1 v/v mixture of cyclohexane and diethyl ether as eluent. There was thus obtained 10-(dimethyl-t-butylsilyloxy)dec-1-yne.

EXAMPLE 2

The process described in Example 1 was repeated except that the appropriate (1RS,2RS)-1,2,3,4-tetrahydro-1-(10-mesyloxydecyl)-2-phenyl-6-methoxynaphthalene and hexanethiol were used as starting materials. There were thus obtained as oils the compounds described in the following table, the structures of all of which were confirmed by proton magnetic resonance and mass spectroscopy:

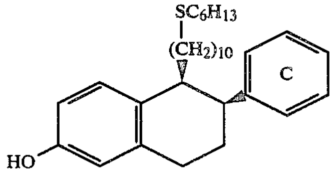

| Substituent in Ring C |
|---|
| None |
| 3-chloro |
| 4-chloro |
| 2-methyl |
| 3-methyl |
| 4-methyl |
| 2,4-dimethyl |
| 4-ethyl |
| 4-isopropyl |
| 4-isobutyl |
| 3-trifluoromethyl |
| 4-(1-hydroxyethyl)* |
| 4-acetyl** |
| 4-dimethylsulphamoyl |
| 4-(2,2,2-trifluoro-1-hydroxy-1- |

-continued

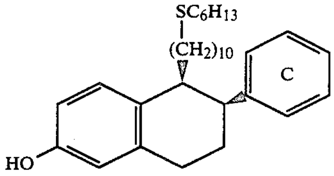

| Substituent in Ring C |
|---|
| trifluoromethylethyl)-** |

Except as stated, the starting materials were obtained by a similar process to that described in Example 1 using the appropriate phenylacetic acid in place of p-fluorophenylacetic acid as initial starting material.
*The corresponding 4-acetyl compound (as the final hexylthio derivative) was reduced to the corresponding 4-(1-hydroxyethyl) compound with sodium borohydride in ethanol.
**The starting material was obtained by a Friedel-Kraft reaction of 1,2,3,4-tetrahydro-6-methoxy-2-phenylnaphth-1-one with acetyl chloride or hexafluoroacetone respectively and aluminium chloride in methylenechloride.

Except as stated, the starting materials were obtained by a similar process to that described in Example 1 using the appropriate phenylacetic acid in place of p-fluorophenylacetic acid as initial starting material. * The corresponding 4-acetyl compound (as the final hexylthio derivative) was reduced to the corresponding 4-(1-hydroxyethyl) compound with sodium borohydride in ethanol. ** The starting material was obtained by a Friedel-Kraft reaction of 1,2,3,4-tetrahydro-6-methoxy-2-phenylnaphth1-one with acetyl chloride or hexafluoroacetone respectively and aluminium chloride in methylene chloride.

EXAMPLE 3

2,3-Dichloro-5,6-dicyano-1,4-benzoquinone (0.12 g.) was added to a stirred solution of (1RS, 2RS) -2-p-fluorophenyl-1-(10-hexylthiodecyl)-1,2,3,4-tetra -hydro-6-methoxynaphthalene (Example 1; 0.11 g.) in toluene (10 ml.) and the mixture was stirred and heated under reflux for 1 hour and then evaporated to dryness. The residue was purified by chromatography on a silica gel column using toluene as eluant and there was thus obtained 2-p-fluorophenyl-1-(10-hexylthiodecyl)-6-methoxynaphthalene.

The above compound was treated with boron tribromide by a similar process to that described in the second paragraph of Example 1, and there was thus obtained as an oil 2-p-fluorophenyl-1-(10-hexylthiodecyl)naphth-6-ol, the structure of which was confirmed by proton magnetic resonance and mass spectroscopy.

EXAMPLE 4

A solution of sodium metaperiodate (0.03 g.) in water (1 ml.) was added to a stirred solution of (1RS, 2RS)-2-p-fluorophenyl-1-(10-hexylthiodecyl) -1,2,3,4-tetrahydronaphth-6-ol (Example 1; 0.06 g.) in methanol (5 ml.) and the mixture was stirred at laboratory temperature for 16 hours. The methanol was removed by evaporation and the residue was extracted three times with ethyl acetate (10 ml. each time). The combined extracts were washed with water, dried and evaporated to dryness and the residue was purified by chromatography on a silica gel column using a 4:1 v/v mixture of toluene and ethyl acetate as eluent. There was thus obtained (1RS, 2RS)-2-p-fluorophenyl-1-(10-hexylsulphinyldecyl)-1,2 3,4-tetrahydronaphth-6-ol, the structure of which was confirmed by proton magnetic resonance and mass spectroscopy.

The process described above was repeated using the appropriate hexylthiodecyl compound described in Example 2, and there were thus obtained the compounds described in the following table:

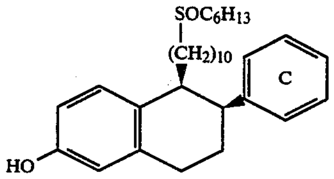

| Substituent in Ring C |
|---|
| None |
| 4-chloro |
| 2-methyl |
| 3-methyl |
| 4-methyl |
| 2,4-dimethyl |
| 4-ethyl |
| 4-isopropyl |
| 4-isobutyl |
| 3-trifluoromethyl |
| 4-dimethylsulphamoyl |

EXAMPLE 5

The process described in Example 1 was repeated using the appropriate (1RS, 2RS)-1,2,3,4-tetrahydro-1-(omega-mesyloxyalkyl)-6-methoxy-2-(substituted phenyl)naphthalene and the appropriate thiol as starting materials. There were thus obtained as oils the compounds described in the following table, the structure of all of which were confirmed by proton magentic resonance and mass spectroscopy:

TABLE I

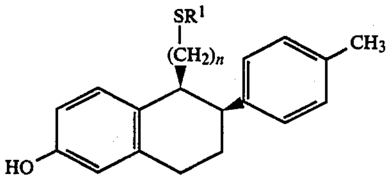

| n | $R^1$ |
|---|---|
| 8 | 6,6,6-trifluorohexyl |
| 9 | n-hexyl |
| 9 | 4,4,4-trifluorobutyl |
| 9 | 5,5,5-trifluoropentyl |
| 9 | 4,4,5,5,5-pentafluoropentyl |
| 9 | 1H,1H,2H,2H—heptafluoropentyl |
| 9 | 6,6,6-trifluorohexyl |
| 9 | 5,5,6,6,6-pentafluorohexyl |
| 9 | 4,4,5,5,6,6,6-heptafluorohexyl |
| 9 | 1H,1H,2H,2H—nonafluorohexyl |
| 9 | 5,5,6,6,7,7,7-heptafluoroheptyl |
| 9 | 3-(1,1,2,2-tetrafluoroethoxy)propyl |
| 9 | p-trifluoromethylbenzyl |
| 10 | 4,4,4-trifluorobutyl |
| 10 | 5,5,5-trifluoropentyl |
| 10 | 4,4,5,5,5-pentafluoropentyl |
| 10 | 1H,1H,2H,2H—heptafluoropentyl |
| 10 | 6,6,6-trifluorohexyl |
| 10 | 5,5,6,6,6-pentafluorohexyl |
| 10 | 4,4,5,5,6,6,6-heptafluorohexyl |
| 10 | 5,5,6,6,7,7,7-heptafluoroheptyl |
| 10 | 3-(1,1,2,2-tetrafluoroethoxy)propyl |
| 10 | pent-3-ynyl |
| 10 | hex-3-ynyl |
| 10 | p-trifluoromethylbenzyl |

TABLE 2

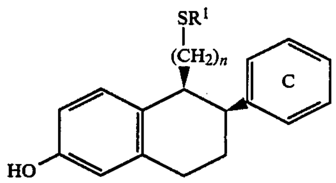

| n | $R^1$ | Substituent in Ring C |
|---|---|---|
| 10 | 4,4,5,5,5-pentafluoro-pentyl | 2-methyl |
| 10 | 4,4,5,5,6,6,6-heptafluorohexyl | 2-methyl |
| 10 | 4,4,5,5,6,6,6-heptafluorohexyl | 4-dimethyl-sulphamoyl |
| 9 | 4,4,5,5,5-pentafluoropentyl | 2-chloro |
| 9 | 7,7,7-trifluoroheptyl | 2-chloro |

The starting materials were obtained by a similar process to that described in Example 1, using the appropriately substituted phenylacetic acid and 2-m-methoxyphenylethyl methanesulphonate as initial starting materials, and either 10-(dimethyl-t-butylsilyloxy)dec-1-yne, 9-(dimethyl-t-butylsilyloxy)non-1-yne or 8-(dimethyl-t-butyl-silyloxy)oct-1-yne (the last two compounds being (prepared from 7-bromoheptanol or 6-bromohexanol respectively by a similar process to that described in the last paragraph of Example 1) as later intermediates.

EXAMPLE 6

The process described in Example 3 was repeated using the appropriate 6-methoxytetrahydro-naphthalene (the penultimate product in the preparation of the compounds described in Example 5) as starting material. There were thus obtained the compounds described in the following table, the structures of all of which were confirmed by proton magnetic resonance and mass spectroscopy:

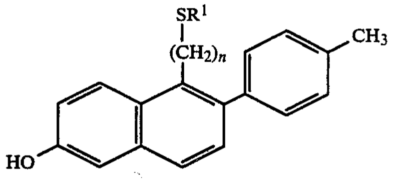

| n | $R^1$ |
|---|---|
| 8 | 6,6,6-trifluorohexyl |
| 9 | n-hexyl |
| 9 | 4,4,4-trifluorobutyl |
| 9 | 5,5,5-trifluoropentyl |
| 9 | 4,4,5,5,5-pentafluoropentyl |
| 9 | 1H,1H,2H,2H—heptafluoropentyl |
| 9 | 6,6,6-trifluorohexyl |
| 9 | 5,5,6,6,6-pentafluorohexyl |
| 9 | 4,4,5,5,6,6,6-heptafluorohexyl |
| 9 | 1H,1H,2H,2H—nonafluorohexyl |
| 9 | 5,5,6,6,7,7,7-heptafluoroheptyl |
| 9 | 3-(1,1,2,2-tetrafluoroethoxy)propyl |
| 9 | p-trifluoromethylbenzyl |
| 10 | n-hexyl |
| 10 | 4,4,4-trifluorobutyl |
| 10 | 5,5,5-trifluoropentyl |
| 10 | 4,4,5,5,5-pentafluoropentyl |
| 10 | 1H,1H,2H,2H—heptafluoropentyl |
| 10 | 6,6,6-trifluorohexyl |
| 10 | 5,5,6,6,6-pentafluorohexyl |
| 10 | 4,4,5,5,6,6,6-heptafluorohexyl |
| 10 | 5,5,6,6,7,7,7-heptafluoroheptyl |

-continued

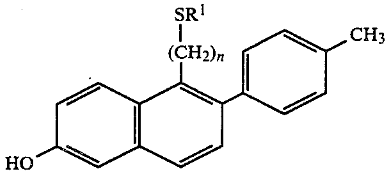

| n | $R^1$ |
|---|---|
| 10 | 3-(1,1,2,2-tetrafluoroethoxy)propyl |
| 10 | pent-3-ynyl |
| 10 | hex-3-ynyl |
| 10 | p-trifluoromethylbenzyl |

EXAMPLE 7

Aqueous 1ON-sodium hydroxide solution (0.08 ml.) was added to a solution of p-[(1RS,2RS)-1-(10- mesyloxydecyl)-6-methoxy-1,2,3,4-tetrahydronaphth-2-yl]-N,N-dimethylbenzamide (0.107 g.) and S-n-hexylisothiourea hydrobromide (0.097 g.) in dimethylformamide (5 ml.) and the mixture was stirred at laboratory temperature for 2 hours and then evaporated to dryness. Water (5 ml.) was added to the residue and the mixture was extracted three times with diethyl ether (10 ml. each time). The combined extracts were dried and evaporated to dryness and the residue was purified by chromatography on a silica gel column using initially cyclohexane and then toluene as eluent. The product thus obtained was demethylated with boron tribromide by a similar process to that described in the second paragraph of Example 1, and the product was purified by chromatography on a silica gel column using a 4:4 v/v mixture of toluene and ethyl acetate as eluent. There was thus obtained as an oil p-[(1RS,2RS)-1-(10-hexylthiodecyl)-6-hydroxy-1,2,3,4-tetrahydronaphth-2-yl]-N,N-dimethylbenzamide, the structure of which was confirmed by proton magnetic resonance and mass spectroscopy.

The starting material was obtained as follows:

n-Butyl-lithium (59 ml. of a 1.6 molar solution in hexane) was added to a stirred solution of p-bromophenyldimethoxymethane (21.8 g.) in tetrahydrofuran (200 ml.) which was maintained at −78° C., and the mixture was stirred at that temperature for 2 hours. A solution of 2-chloro-1,2,3,4-tetrahydro-6-methoxynaphthalen-1-one (12.8 g.) in tetrahydrofuran (100 ml.) was added and the mixture was allowed to warm up to laboratory temperature and was stirred at that temperature for 2 hours and then evaporated to dryness. Water (100 ml.) was added and the mixture was extracted three times with ethyl acetate (100 ml. each time). The combined extracts were washed with saturated aqueous ammonium chloride solution and then with water, dried and evaporated to dryness and the residue was purified by chromatography on a silica gel column using a 19:1 v/v mixture of toluene and ethyl acetate as eluent.

A solution of phenyl magnesium chloride (21.5 ml. of a 2-molar solution in tetrahydrofuran) was added to a stirred solution of the 2-chloro-1-(p-dimethoxymethylphenyl)-1,2,3,4-tetrahydro-6-methoxynaphth-1-ol thus obtained (11.9 g.) in tetrahydrofuran (150 ml.) and the mixture was stirred and heated at 50° C. for 16 hours. Saturated aqueous ammonium chloride solution (200 ml.) was added and the mixture was extracted three times with ethyl acetate (50 ml.) each time). The combined extracts were washed with water, dried and evaporated to dryness and the residue was purified by chromatography on a silica gel column using a 19:1 v/v mixture of methylene chloride and ethyl acetate as eluent.

A mixture of the 2-(p-dimethoxymethylphenyl)-1,2,3,4-tetrahydro-6-methoxynaphthalen-1-one thus obtained (2.5 g.), tetrahydrofuran (25 ml.), acetic acid (50 ml.) and water (25 ml.) was kept at 50° C. for 3 hours and then evaporated to dryness. There was thus obtained 2-(p-formylphenyl)-1,2,3,4-tetrahydro-6-methoxynaphthalen-1-one.

8N-Aqueous chromic acid solution (Jones' reagent, 1 ml.) was added dropwise to a stirred solution of the above naphthalone (0.664 g.) in acetone (20 ml.) which was cooled to −20° C. and the mixture was allowed to warm up to laboratory temperature and stirred at that temperature for 1 hour. Isopropanol (0.1 ml.) was added and the mixture was evaporated to dryness. Water (15 ml.) was added and the mixture was extracted three times with ethyl acetate (10 ml. each time). The combined extracts were washed with water, dried and evaporated to dryness and there was thus obtained as residue p-(6-methoxy-1-oxo-1,2,3,4-tetrahydronaphth-2-yl)benzoic acid.

Oxalyl chloride (1.6 ml.) was added to a stirred solution of the above acid (3.6 g.) and dimethylformamide (0.05 ml.) in methylene chloride (100 ml.) and the mixture was stirred at laboratory temperature for 16 hours and then evaporated to dryness. A solution of the residue in methylene chloride (50 ml.) was added dropwise to a 25% w/v solution of dimethylamine in tetrahydrofuran (10 ml.) which was maintained at 0° C., and the mixture was allowed to warm up to laboratory temperature, stirred at that temperature for 2 hours and then evaporated to dryness. Water (20 ml) was added and the mixture was extracted three times with ethyl acetate (50 ml. each time). The combined extracts were washed with water, dried and evaporated to dryness and the residue was purified by chromatography on a silica gel column using ethyl acetate as eluent.

The p-(6-methoxy-1-oxo-1,2,3,4-tetrahydronaphth-2-yl)-N-N-dimethylbenzamide thus obtained was successively reacted with 10-(dimethyl-t-butylsilyloxy)dec-1-yne, hydrogenated, hydrolysed and reacted with methanesulphonyl chloride by similar processes to those described in the penultimate three paragraphs of Example 1, and there was thus obtained p-[(1RS, 2RS)-1-(10-mesyloxydecyl)-6-methoxy-1,2,3,4-tetrahydronaphth-2-yl]-N,N-dimethylbenzamide.

EXAMPLE 8.

Aqueous 2N-sodium hydroxide solution (10 ml.) was added to a solution of p-[(1RS, 2RS)-1-(10-hexylthiodecyl)-6-hydroxy-1,2,3,4-tetrahydronaphth-2-yl]-N,N-dimethylbenzamide (Example 7; 0.24 g.) in ethanol (10 ml.) and the mixture was heated under reflux for 16 hours. The ethanol was removed by evaporation and the residue was acidified to pH 1 with aqueous 2N-hydrochloric acid and extracted three times with ethyl acetate (15 ml. each time). The combined extracts were washed with water, dried and evaporated to dryness and the residue was purified by chromatography on a silica gel column using a 4:1 v/v mixture of toluene and ethyl acetate as eluent. There was thus obtained as an oil p-[(1RS, 2RS)-1-(10-hexylthiodecyl)-6-hydroxy-1,2,3,4-tetrahydronaphth-2-yl]benzoic acid, the structure of which was confirmed by proton magnetic resonance and mass spectroscopy.

EXAMPLE 9

Borane (0.4 ml. of molar solution in tetrahydrofuran) was added to a stirred solution of p-[(1RS, 2RS)-1-(10-hexylthiodecyl)-6-hydroxy-1,2,3,4-tetrahydronaphth-2-yl]benzoic acid (Example 8; 0.063 g.) in tetrahydrofuran (3 ml.) and the mixture was stirred at laboratory temperature for 16 hours. Water (10 ml.) was added and the mixture was acidified to pH 1 with aqueous 2N-hydrochloric acid and extracted three times with ethyl acetate (10 ml. each time). The combined extracts were washed with water, dried and evaporated to dryness and the residue was purified by chromatography on a silica gel column using a 7:1 v/v mixture of toluene and ethyl acetate as eluent. There was thus obtained (1RS, 2RS)-1-(10-hexylthiodecyl)-2-p-hydroxymethylphenyl-1,2,3,4-tetrahydronaphth-6-ol, the structure of which was confirmed by proton magnetic resonance and mass spectrocopy.

EXAMPLE 10

A mixture of trifluoroacetic anhydride (0.1 ml.), p-[(1RS, 2RS)-6-methoxy-1-(10-{4,4,5,5,5-pentafluoropentyl}thiodecyl)-1,2,3,4-tetrahydronaphth -2-yl]benzamide (0.083 g.), pyridine (0.1 ml.) and dioxan (5 ml.) was stirred at laboratory temeperature for 2 hours and then evaporated to dryness. Water (5 ml.) was added and the mixture was extracted three times with methylene chloride (10 ml. each time). The combined extracts were washed with water. dried and evaporated to dryness and the residue was purified by chromatography on a silica gel column using a 3:1 v/v mixture of toluene and petroleum ether (b.p. 40°-60° C.) as eluent. The product thus obtained was demeth-lyated with boron tribromide by a similar process to that described in the second paragraph of Example 1, and there was thus obtained p-[(1RS, 2RS)-6-hydroxy-1-(10-{4,4,5,5,5-pentafluoropentyl}thiodecyl)-1,2,3,4-tetrahydronaphth-2-yl]benzonitrile, the structure of which was confirmed by proton magnetic resonance and mass spectrocopy.

The benzamide used as starting material was obtained by reacting p-[(1RS, 2RS)-1-(10-mesyloxydecyl)-6-methoxy-1,2,3,4-tetrahydronaphth-2-yl]-N,N-dimethylbenzamide (Example 7) with S-(4,4,5,5,5-pentafluoropentyl)isothiourea hydrobromide by a similar process to that described in Example 7, hydrolysing the dimethylamide to the carboxylic acid by a similar process to that described in Example 8, and reacting the acid with oxalyl chloride and ammonia by a similar process to that described in the penultimate paragraph of Examaple 7 using a solution of ammonia in tetrahydrofuran in place of dimethylamine.

EXAMPLE 11

The process described in Example 4 was repeated using the appropriate thio compound described in any of Examples 5 to 10 as starting materials and there were thus obtained the compounds described in the following tables:

TABLE 1

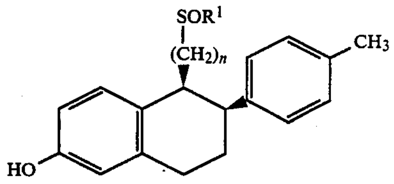

| n | $R^1$ |
|---|---|
| 8 | 6,6,6-trifluorohexyl |
| 9 | 4,4,4-trifluorobutyl |
| 9 | 5,5,5-trifluoropentyl |
| 9 | 4,4,5,5,5-pentafluoropentyl |
| 9 | 1H,1H,2H,2H—heptafluoropentyl |
| 9 | 6,6,6-trifluorohexyl |
| 9 | 5,5,6,6,6-pentafluorohexyl |
| 9 | 4,4,5,5,6,6,6-heptafluorohexyl |
| 9 | 5,5,6,6,7,7,7-heptafluoroheptyl |
| 9 | n-hexyl |
| 9 | p-trifluoromethylbenzyl |
| 10 | 4,4,4-trifluorobutyl |
| 10 | 5,5,5-trifluoropentyl |
| 10 | 4,4,5,5,5-pentafluoropentyl |
| 10 | 1H,1H,2H,2H—heptafluoropentyl |
| 10 | 6,6,6-trifluorohexyl |
| 10 | 5,5,6,6,6-pentafluorohexyl |
| 10 | 4,4,5,5,6,6,6-heptafluorohexyl |
| 10 | 5,5,6,6,7,7,7-heptafluoroheptyl |
| 10 | p-trifluoromethylbenzyl |

TABLE 2

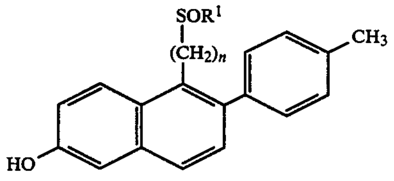

| n | $R^1$ |
|---|---|
| 8 | 6,6,6-trifluorohexyl |
| 9 | n-hexyl |
| 9 | 4,4,4-trifluorobutyl |
| 9 | 5,5,5-trifluoropentyl |
| 9 | 4,4,5,5,5-pentafluoropentyl |
| 9 | 1H,1H,2H,2H—heptafluoropentyl |
| 9 | 6,6,6-trifluorohexyl |
| 9 | 5,5,6,6,6-pentafluorohexyl |
| 9 | 4,4,5,5,6,6,6-heptafluorohexyl |
| 9 | 1H,1H,2H,2H—nonafluorohexyl |
| 9 | 5,5,6,6,7,7,7-heptafluoroheptyl |
| 9 | 3-(1,1,2,2-tetrafluoroethoxy)propyl |
| 9 | p-trifluoromethylbenzyl |
| 10 | n-hexyl |
| 10 | 4,4,4-trifluorobutyl |
| 10 | 5,5,5-trifluoropentyl |
| 10 | 4,4,5,5,5-pentafluoropentyl |
| 10 | 1H,1H,2H,2H—heptafluoropentyl |
| 10 | 6,6,6-trifluorohexyl |
| 10 | 5,5,6,6,6-pentafluorohexyl |
| 10 | 4,4,5,5,6,6,6-pentafluorohexyl |
| 10 | 5,5,6,6,7,7,7-heptafluoroheptyl |
| 10 | 3-(1,1,2,2-tetrafluoroethoxy)propyl |
| 10 | pent-3-ynyl |
| 10 | hex-3-ynyl |
| 10 | p-trifluoromethylbenzyl |

TABLE 3

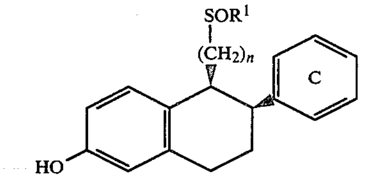

| $R^1$ | n | Substituent in Ring C |
|---|---|---|
| n-Hexyl | 10 | 4-CON($CH_3$)$_2$ |
| n-Hexyl | 10 | 4-COOH |
| n-Hexyl | 10 | 4-$CH_2OH$ |
| 4,4,5,5,5-pentafluoropentyl | 10 | 4-CN |
| 4,4,5,5,5-pentafluoropentyl | 10 | 4-$CONH_2$ |
| 4,4,5,5,5-penta fluoropentyl | 10 | 2-$CH_3$ |
| 4,4,5,5,6,6,6-heptafluorohexyl | 10 | 2-$CH_3$ |
| 4,4,5,5,6,6,6-heptafluorohexyl | 10 | 4-$SO_2$($CH_3$)$_2$ |
| 4,4,5,5,5-penta-fluoropentyl | 9 | 2-Cl |
| 7,7,7-trifluoro-heptyl | 9 | 2-Cl |

EXAMPLE 12 m-Chloroperbenzoic acid (0.035 g.) was added to a stirred solution of 1-[10-(4,4,5,5,5-pentafluoropentyl)-thiodecyl]-2-p-tolylnaphth-6-ol (Example 6; 0.044 g.) in methylene chloride (5 ml.) and the mixture was stirred at laboratory temperature for 1 hour, diluted with methylene chloride (5 ml.), washed with saturated aqueous sodium bicarbonate solution and then with water (10 ml. each), dried and evaporated to dryness. The residue was purified by chromatography on a silica gel column using a 3:1 v/v mixture of toluene and ethyl acetate as eluent, and there was thus obtained 1-[10-(4,4,5,5,5-pentafluoropentyl)sulphonyldecyl]-2-p-tolylnaphth-6-ol, the structure of which was confirmed by proton magnetic resonance and mass spectrocopy.

EXAMPLE 13

Aqueous 2N-sodium hydroxide solution (2 ml.) was added to a solution of a mixture of the (1RS,2RS)-and (1RS,2SR)- isomers of 1,2,3,4-tetrahydro-1-(10-mesyloxydecyl)-2-p-methoxyphenyl-2,6-dimethylnaphthalene (0.52 g.) and 5-(4,4,5,5,5-pentafluoropentyl)isothiouronium tosylate (0.82 g.) in dimethylformamide (10 ml.) and the mixture was stirred at laboratory temperature for 2 hours. Water (50 ml.) was added and the mixture was extracted three times with ethyl acetate (50 ml. each time). The combined extracts were dried and evaporated to dryness, and the residue was demethylated with boron tribromide by a similar process to that described in the second paragraph of Example 1. The final product was purified by chromatography on a silica gel column using a 99:1 v/v mixture of toluene and ethyl acetate as eluent. There were thus separately obtained as oils the (1RS,2RS)- and (1RS,2SR)- isomers of 4-[2,6-dimethyl-1-{10-(4,4,5,5,5-pentafluoropentylthio)decyl}-1,2,3,4-tetrahydronaphth-2-yl]phenol, the structures of both of which isomers were confirmed by proton magnetic resonance and mass spectroscopy.

The mixture of isomers used as starting material was obtained as follows:

The process described in the third and fourth paragraphs of Example 1 was repeated using p-methoxyphenylacetic acid and 2-m-tolylethyl methanesulphonate as starting materials. The 3,4-dihydro-2-p-methoxyphenyl-6-methylnaphthalen-1(2H)-one thus obtained (1.33 g., m.p. 125°-126° C. after crystallisation from methanol) was added to a stirred solution of lithium diisopropylamide in tetrahydrofuran [prepared from n-butyllithium (5 ml. of a 1.5 molar solution in hexane) and a solution of diisopropylamine (0.8 g.; freshly distilled from potassium hydroxide) in tetrahydrofuran (20 ml.)] which was cooled to −20° C. under an atmosphere of argon. The mixture was stirred at −20° C. for 1 hour, methyl iodide (1.27 g.) was added and the mixture was stirred at laboratory temperature for 18 hours. Aqueous N-hydrochloric acid (50 ml.) was added and the mixture was extracted twice with diethyl ether (50 ml. each time). The combined extracts were dried and evaporated to dryness and the residue was purified by medium pressure chromatography on a silica gel column using a 12.5:1 v/v mixture of petroleum ether (b.p. 60°-80° C.) and ethyl acetate as eluent. The product was crystallised from petroleum ether (b.p. 60°-80° C.) and there was thus obtained 3,4-dihydro-2-p-methoxyphenyl-2,6-dimethylnaphthalen-1(2H)-one, m.p. 80°-82° C.

This product was then successively reacted with 10-(dimethyl-t-butylsilyloxy)dec-1-yne, hydrogenated over a palladium-on-charcoal catalyst, hydrolysed and reacted with methanesulphonyl chloride by similar processes to those described in the fifth, sixth and seventh paragraphs of Example 1. There was thus obtained the desired mixture of (1RS,2RS)- and (1RS,2SR)-isomers of 1,2,3,4-tetrahydro-1-(10-mesyloxydecyl)-2-p-methoxyphenyl-2,6-dimethylnaphthalene.

The process described above was repeated using the appropriate phenylacetic acid, the appropriate phenethyl mesylate and the appropriate silyloxyalk-1-yne as intermediates, and there was thus obtained as oils the compounds described in the following table, the structures of all of which were confirmed by proton magnetic resonance and mass spectroscopy:

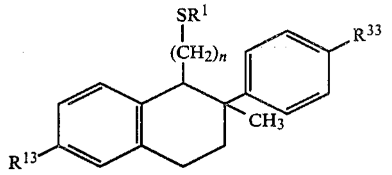

| $R^{13}$ | $R^{33}$ | n | $R^1$ | Isomer |
|---|---|---|---|---|
| $CH_3$ | OH | 10 | n-pentyl | 1RS,2RS |
| $CH_3$ | OH | 10 | n-pentyl | 1RS,2SR |
| Cl | OH | 9 | $(CH_2)_3CF_2CF_2CF_3$ | 1RS,2RS |
| H | OH | 9 | $(CH_2)_3CF_2CF_2CF_3$ | 1RS,2RS |
| H | OH | 9 | $(CH_2)_3CF_2CF_2CF_3$ | 1RS,2SR |
| H | H | 9 | $(CH_2)_3CF_2CF_3$ | (Mixture)* |
| H | H | 9 | $(CH_2)_3CF_2CF_2CF_3$ | (Mixture)* |
| H | H | 9 | $(CH_2)_3OCF_2CHF_2$ | (Mixture)* |
| HO | $CH_3$ | 10 | n-hexyl | (Mixture) |
| HO | H | 9 | $(CH_2)_3CF_2CF_3$ | (Mixture) |

*The demethylation process using boron tribromide was omitted as there was no methoxy group to demethylate.

EXAMPLE 14

The process described in Example 4 was repeated using the compounds described in Example 13 as starting materials. There were thus obtained as oils the compounds described in the following table, the structures of all of which were confirmed by proton magnetic resonance and mass spectroscopy:

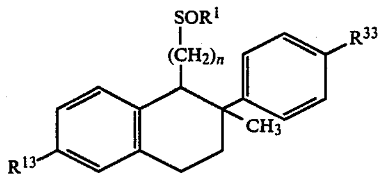

| $R^{13}$ | $R^{33}$ | n | $R^1$ | Isomer |
|---|---|---|---|---|
| $CH_3$ | OH | 10 | $(CH_2)_3CF_2CF_3$ | 1RS,2RS |
| $CH_3$ | OH | 10 | $(CH_2)_3CF_2CF_3$ | 1RS,2SR |
| $CH_3$ | OH | 10 | n-pentyl | 1RS,2RS |
| $CH_3$ | OH | 10 | n-pentyl | 1RS,2SR |
| Cl | OH | 9 | $(CH_2)_3CF_2CF_2CF_3$ | 1RS,2RS |
| H | OH | 9 | $(CH_2)_3CF_2CF_2CF_3$ | 1RS,2RS |
| H | OH | 9 | $(CH_2)_3CF_2CF_2CF_3$ | 1RS,2SR |
| H | H | 9 | $(CH_2)_3CF_2CF_3$ | 1RS,2RS |
| H | H | 9 | $(CH_2)_3CF_2CF_3$ | 1RS,2SR |
| H | H | 9 | $(CH_2)_3CF_2CF_2CF_3$ | (Mixture) |
| H | H | 9 | $(CH_2)_3OCF_2CHF_2$ | (Mixture) |
| HO | $CH_3$ | 10 | n-hexyl | (Mixture) |
| HO | H | 9 | $(CH_2)_3CF_2CF_3$ | (Mixture) |

EXAMPLE 15

The process described in Example 12 was repeated using some of the compounds described in Example 13 as starting materials. There were thus obtained as oils the compounds described in the following table, the structures of all of which were confirmed by proton magnetic resonance and mass spectroscopy:

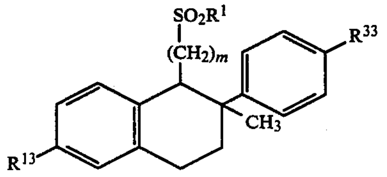

| $R^{13}$ | $R^{33}$ | n | $R^1$ | Isomer |
|---|---|---|---|---|
| H | H | 9 | $(CH_2)_3CF_2CF_3$ | (Mixture) |
| H | H | 9 | $(CH_2)_3CF_2CF_2CF_3$ | (Mixture) |
| H | H | 9 | $(CH_2)_3OCF_2CHF_2$ | (Mixture) |
| HO | H | 9 | $(CH_2)_3CF_2CF_3$ | 1RS,2RS |

EXAMPLE 16

Aqueous 10N-sodium hydroxide solution (0.15 ml.) was added to a stirred solution of 1-(10-bromodecyl)-2-phenylnaphth-6-ol (0.09 g.) and S-(4,4,5,5,5-pentafluoropentyl)isothiouronium tosylate (0.25 g.) in dimethylformamide (3 ml.) which was maintained under an atmosphere of argon, and the mixture was stirred at laboratory temperature for 18 hours, acidified with aqueous N-hydrochloric acid (20 ml.) and extracted twice with diethyl ether (20 ml. each time). The combined extracts were dried and evaporated to dryness and the product obtained was oxidised with sodium metaperiodate by a similar process to that described in Example 4. There was thus obtained as an oil 1-[10-(4,4,5,5,5-pentafluoropentylthio)decyl]-2-phenylnaphth-6-ol, the structure of which was confirmed by proton magnetic resonance and mass spectroscopy.

The naphthol starting material was obtained as follows:

The processes described in the third, fourth and fifth paragraphs of Example 1 were repeated using phenylacetic acid in place of p-fluorophenylacetic acid as starting material. The tetrahydronaphthyl group was aromatised to a naphthyl group with 2,3-dichloro-5,6-dicyano- 1,4-benzoquinone by a similar process to that described in Example 3, and the silyloxy group was removed by hydrolysis, the acetylene group was hydrogenated and the decanol was mesylated, in that order, by similar processes to those described respectively in the sixth (second part), sixth (first part) and seventh paragraphs of Example 1.

Boron tribromide (3.6 ml. of a molar solution in methylene chloride) was added to a stirred solution of the 1-(10-mesyloxydecyl)-6-methoxy-2-phenylnaphthalene thus obtained (0.4 g.) in methylene chloride (10 ml.) which was maintained at −70° C. under an atmosphere of argon, and the mixture was allowed to warm up to laboratory temperature, kept at that temperature for 2 hours, and saturated aqueous sodium bicarbonate solution (10 ml.) was then added. The mixture was extracted twice with diethyl ether (20 ml. each time) and the combined extracts were dried and evaporated to dryness. There was thus obtained 1-(10-bromodecyl)-2-phenylnaphth-6-ol which was used without further purification.

EXAMPLE 17

A mixture of (1RS,2RS)-1,2,3,4-tetrahydro-1-(10-mesyloxydecyl)-6-methoxy-2-p-tolylnaphthalene (0.055 g.), butylmethylphenylphosphine (0.225 ml.), sodium iodide (0.172 g.) and acetonitrile (25 ml.) was heated under reflux for 16 hours and then evaporated to dryness. The residue was purified by chromatography on a silica gel column using a 4:1 v/v mixture of cyclohexane and methylene chloride as eluent. A mixture of a solution of the butyl{[(1RS,2RS)-6-methoxy-1,2,3,4-tetrahydro-2-p-tolylnaphth-1-yl]decyl}methylphenylphosphonium iodide thus obtained (0.45 g.) in tetrahydrofuran (30 ml.), aqueous 30% sodium hydroxide solution (10 ml.) and tetrabutylammonium bromide (0.02 g.) was stirred at laboratory temperature for 2 days, diluted with water (50 ml.) and extracted three times with ethyl acetate (20 ml. each time). The combined extracts were washed with water, dried and evaporated to dryness and the residue was purified by chromatography on a silica gel column using a 24:1 v/v mixture of methylene chloride and methanol as eluent.

The product obtained was demethylated with boron tribromide by a similar process to that described in the second paragraph of Example 1, and the final product was purified by chromatography on a silica gel column using a 24:1 v/v mixture of methylene chloride and methanol as eluent. There was thus obtained as an oil (1RS,2RS)-1-(10-butylmethylphosphinyldecyl)-1,2,3,4-tetrahydro-2-p-tolylnaphth-6-ol, the structure of which was confirmed by proton magnetic resonance and mass spectroscopy.

What we claim is:

1. A phenol compound of the formula:

$$NU{-}A{-}X{-}R^1$$

where NU is a phenolic nucleus of the general formula

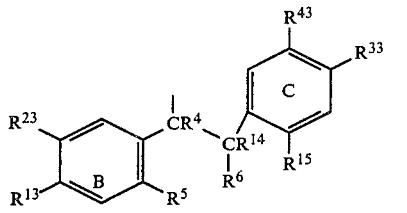

wherein one of $R^{13}$ and $R^{23}$, or one of $R^{33}$ and $R^{43}$, has the formula $R^3O$—, wherein $R^3$ is hydrogen or alkyl, cycloalkyl, alkanoyl, alkoxycarbonyl, carboxyalkanoyl or aroyl each of up to 10 carbon atoms;

wherein one of $R^{13}$ and $R^{23}$, or one of $R^{33}$ and $R^{43}$, which is in the other aromatic ring B or C from that which contains the $R^3O$—substituent, is hydrogen, halogen, amino, trifluoromethyl, cyano, carboxy or carbamoyl, or alkyl, hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl each of up to 6 carbon atoms, and wherein the other two of $R^{13}$, $R^{23}$, $R^{33}$, and $R^{43}$ are hydrogen; or wherein one of $R^{13}$ and $R^{23}$, and one of $R^{33}$ and $R^{43}$, is hydrogen, halogen, amino, trifluoromethyl, cyano, carboxy or carbamoyl, or alkyl, hydroxyalkyl, hydroxyfluoroalkyl, alkylamino, dialkylamino, alkanoylamino, alkanoyl, alkoxycarbonyl, alkylcarbamoyl, dialkylcarbamoyl, alkylsulphamoyl or dialkylsulphamoyl each of up to 6 carbon atoms; and wherein the other of $R^{13}$ and $R^{23}$, and the other of $R^{33}$ and $R^{43}$, is hydrogen;

wherein $R^4$ and $R^{14}$, which may be the same or different, each is hydrogen or alkyl of up to 5 carbon atoms, or $R^4$ and $R^{14}$ are joined together so that $CR^4$—$CR^{14}$ is an olefinic double bond;

wherein $R^5$ and $R^6$ together form a direct link or —$CH_2$—, —$CH(CH_3)$—, —$CH_2CH_2$—, —$(CH_2)_3$—, or —CH=CH—, and $R^{15}$ is hydrogen;

and wherein the aromatic ring B and C each is unsubstituted or substituted with one or more halogen or methyl, ethyl, isopropyl or isobutyl substituents;

wherein A is straight- or branched-chain alkylene, alkenylene or alkynylene each of from 4 to 12 carbon atoms; or A has the formula:

$$—A^1—Y^3—A^{21}—$$

wherein $A^1$ is alkylene or alkenylene and $A^{21}$ is a direct link or alkylene, alkenylene or cycloalkylene, such that $A^1$ and $A^{21}$ together have a total of 2 to 10 carbon atoms, and $Y^3$ is phenylene or napthylene which is unsubstituted or substituted with one or more halogen or methyl, ethyl, isopropyl or isobutyl substituents, wherein $R^1$ is alkyl, alkenyl, alkynyl, cycloalkyl, halogenoalkyl, alkoxyalkyl, haloagenoalkoxyalkyl each of up to 10 carbon atoms, or, phenyl, chlorophenyl, o-ethylphenyl, p-cyanophenyl, p-hydroxyphenyl, p-methoxyphenyl, alkyl of 1 to 3 carbon atoms which bears a phenyl, tolyl, halogenophenyl or trifluoromethylphenyl substituent, α-methylbenzyl, 3,4-dichlorobenzyl, p-cyanobenzyl or p-methylthiobenzyl and wherein X is —S—, —SO— or —$SO_2$—, or a pharmaceutically acceptable salt of a compound wherein $R^3$ is carboxyalkanoyl.

2. A phenol compound of the formula claimed in claim 1 wherein $R^{15}$, $R^{23}$ and $R^{43}$ are all hydrogen, one of $R^{13}$ and $R^{33}$ is hydrogen, halogen, amino, trifluoromethyl, cyano, carboxy, carbamoyl, alkyl of up to 6 carbon atoms, hydroxymethyl, 1hydroxyethyl, 2,2,2-trifluoro-1-hydroxy-1-trifluoroethyl, ethylamino, dimethylamino, acetamido, formyl, acetyl, propionyl, ethoxycarbonyl, methylcarbamoyl, diethylcarbamoyl, methylsulphamoyl, dimethylsulphamoyl or diethylsulphamoyl and the other of $R^{13}$ and $R^{33}$ has the meaning stated above for $R^{13}$ or $R^{33}$ or has the formula $R^3O$— wherein $R^3$ is hydrogen or alkanoyl or alkoxycarbonyl each of up to 5 carbon atoms; wherein either $R^4$ is hydrogen and $R^{14}$ hydrogen, methyl or ethyl, or $R^4$ and $R^{14}$ are joined together so that $CR^4$—$CR^{14}$ is an olefinic double bond; wherein $R^5$ and $R^6$ together form —$CH_2$—, —$CH(CH_3)$—, —$CH_2CH_2$— or —CH=CH—; wherein the aromatic rings B and C either bear no further substituent or bear one or more fluoro, methyl or ethyl substituents;

wherein the group —A— has the formula $$—(CH_2)_n—$$

wherein n is an integer of from 4 to 12, or has the formula $$—A^1—Y^3—A^{21}—$$

wherein $A^1$ is a straight-chain alkylene or alkenylene each of 2 to 7 carbon atoms, $Y^3$ is phenylene (meta-or para-) and $A^{21}$ is a direct link, methylene, ethylene or trimethylene;

wherein X is —S—, —SO— or —$SO_2$—;

wherein $R^1$ is methyl, ethyl, n-propyl, isopropyl, n-butyl, isobutyl, t-butyl, n-pentyl, isopentyl, t-pentyl, 2,2-dimethylpropyl, 1-methylbutyl, 2-methylbutyl, n-hexyl, 1,1-dimethylbutyl, 1,3-dimethylbutyl, n-heptyl, n-decyl, allyl, pent-3-ynyl, hex-3-ynyl, cyclopentyl, cyclohexyl, 3-ethoxypropyl, phenyl, o-ethylphenyl, p-chlorophenyl, m-chlorophenyl, p-cyanophenyl, p-hydroxyphenyl, p-methoxyphenyl, benzyl, alpha-methylbenzyl, p-chlorobenzyl, p-methylbenzyl, 3,4-dichlorobenzyl, p-cyanobenzyl, p-methylthiobenzyl, p-trifluoromethylbenzyl, phenethyl, p-fluorophenethyl p-chlorophenethyl, 2-chloro-2,2-difluoroethyl, 2,2,2trifluoroethyl, 4,4,4-trifluorobutyl, 1H,1H-heptafluorobutyl, 5,5,5-trifluoropentyl, 4,4,5,5,5-pentafluoropentyl, 1H,1H,2H,2H-heptafluoropentyl, 6,6,6-trifluorohexyl, 5,5,6,6,6-pentafluorohexyl, 4,4,5,5,6,6,6-heptafluorohexyl, 1H,1H,2H,2H-nonafluorohexyl, 5,5,6,6,7,7,7-heptafluoroheptyl or 3-(1,1,2,2-tetrafluoroethoxy)-propyl.

3. A phenol compound of the formula claimed in claim 1 wherein $R^{15}$, $R^{23}$ and $R^{43}$ are all hydrogen, wherein $R^{13}$ is hydroxy, wherein $R^{33}$ has any of the meanings stated in claim 2, other than $R^3O$, wherein either $R^4$ is hydrogen and $R^{14}$ is hydrogen, methyl or ethyl, or $R^4$ and $R^{14}$ are joined together, wherein $R^5$ and $R^6$ together form —$CH_2$—, —$CH_2CH_2$—, —$CH(CH_3)$— or, —CH=CH—, wherein —A— is —$(CH_2)_n$—, wherein n is an integer from 4 to 12, or —A— is

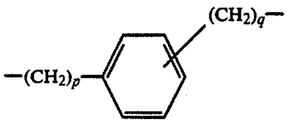

wherein p is an integer from 2 to 7, q is 0 to 3, and the $-(CH_2)_q-$ group is in the meta- or para-position; wherein $R^1$ is alkyl or fluoroalkyl each of 4 to 10 carbon atoms, or phenyl or chlorophenyl, or alkyl of 1 to 3 carbon atoms which bears a phenyl, tolyl, halogenophenyl or trifluoromethylphenyl substituent; wherein X is —S—, —SO— or $-SO_2-$; and wherein ring C is unsubstituted or substituted with one or two methyl substituents.

4. A phenol compound of the formula claimed in claim 1 wherein the number of carbon atoms in the two groups A and $R^1$ adds up to 14 to 16 if neither $R^1$ nor A contains a phenyl or phenylene group, 17 to 19 if there is either a phenylene group in —A— or a phenyl group in $R^1$, and 19 to 21 if there are both a phenylene group in —A— and a phenyl group in $R^1$.

5. A phenol compound as claimed in claim 1 which has the formula $$NU-A-X-R^1$$

wherein NU is 6-hydroxy-2-phenylnaphth-1-yl, 1,2,3,4-tetrahydro-6-hydroxy-2-phenylnaphth-1-yl or 1,2,3,4-tetrahydro-6-hydroxy-2-methyl-2-phenylnaphthl-1-yl wherein the 2-phenyl group is unsubstituted or bears one methyl, ethyl, fluoro, chloro or dimethylsulphamoyl substituent;

wherein A is $-(CH_2)_n-$ wherein n is 8, 9 or 10;

wherein X is —S—, —SO— or $-SO_2-$; and wherein $R^1$ is straight-chain alkyl or fluoroalkyl of 4, 5, 6 or 7 carbon atoms.

6. A pharmaceutical composition having antioestrogenic activity comprising an effective amount of a phenol compound of the formula, claimed in claim 1, together with a pharmaceutically acceptable diluent or carrier.

7. A composition as claimed in claim 6 which contains, in addition to the phenol derivative, an effective amount of one or more antiandrogenic agents, antiprogestational agents or aromatase inhibitors.

8. A method for producing an antioestrogenic effect in a warm-blooded animal in need of such treatment, which comprises administering to said animal an effective amount of at least one phenol compound of the formula claimed in claim 1.

9. The compound (1RS,2RS)-1-(10-hexylsulphinyldecyl)-2-p-tolyl-1,2,3,4-tetrahydronaphth-6-ol, (1RS,2RS)-2p-ethylphenyl-1-(10-hexylsulphinyldecyl)-1,2,3,4-tetrahydronapht-6-ol, (1RS,2RS)-2-p-fluorophenyl-1-(10-hexylsulphinyldecyl)-1,2,3,4-tetrahydronaphth-6-ol, (1RS,2RS)-2-methyl-1-[9-(4,4,5,5,5-pentafluoropentylsulphinyl)nonyl]-2-phenyl-1,2,3,4-tetrahydronaphthalene, 2-p-tolyl-1-[9-(5,5,5-trifluoropentylsulphinyl)nonyl]-naphth-6-ol, 1-[9-(4,4,5,5,5-pentafluoropentylsulphinyl)nony]-2-p-tolylnaphth-6-ol, 1-[9-(1H,1H,2H,2H-heptafluoropentylsulphinyl)nonyl]-2-p-tolylnaphth-6-ol or 1-[9-(3-(1,1,2,2-tetrafluoroethoxy)-propylsulphinyl)nonyl]-2-p-tolylnaphth-6-ol.

* * * * *